United States Patent [19]

Gath et al.

[11] 4,017,482

[45] Apr. 12, 1977

[54] METHOD OF PURIFYING CAPROLACTAM

[75] Inventors: Rudolph Hans Gath, Mannheim; Hugo Fuchs, Ludwigshafen, both of Germany

[73] Assignee: BASF Aktiengesellschaft, Ludwigshafen (Rhine), Germany

[22] Filed: Aug. 11, 1975

[21] Appl. No.: 603,444

[30] Foreign Application Priority Data

Sept. 11, 1974 Germany .......................... 2443341

[52] U.S. Cl. ........................................ 260/239.3 A
[51] Int. Cl.² .................................... C07D 201/16
[58] Field of Search ............................ 260/239.3 A

[56] References Cited

UNITED STATES PATENTS 3,210,338  10/1965  Huber et al. ............... 260/239.3 A

FOREIGN PATENTS OR APPLICATIONS 301,432  11/1954  Switzerland ................ 260/239.2 A
951,519   3/1964  United Kingdom ........ 260/239.3 A Primary Examiner—Henry R. Jiles
Assistant Examiner—Robert T. Bond
Attorney, Agent, or Firm—Johnston, Keil, Thompson & Shurtleff

[57] ABSTRACT

A method of simultaneously purifying crude caprolactams obtained from the Beckmann rearrangement of cyclohexanone oxime in oleum and the gas-phase rearrangement of cyclohexanone oxime in the presence of catalysts. The improvement consists in that the crude caprolactam obtained from the catalytic gas-phase rearrangement is added to the acid rearrangement mixture derived from the Beckmann rearrangement in oleum and the mixture is maintained at temperatures of from 100° to 200° C with thorough mixing, whereupon it is neutralized and worked up. Advantageously, the content of lactam in the catalytic gas-phase rearrangement is from 5 to 30% of the content of lactam in the acid rearrangement mixture obtained from the Beckmann rearrangement.

5 Claims, No Drawings

METHOD OF PURIFYING CAPROLACTAM

Numerous methods of purifying caprolactam have been described. These processes mainly relate to the lactam processes now used industrially, virtually all of which are based on the Beckmann rearrangement of cyclohexanone oxime in sulfuric acid or oleum. Successful use has been made of extraction combined with distillation and, in some cases, a chemical treatment.

For example, Swiss Patent No. 301,432 discloses a process for treating impure lactams with oleum followed by neutralization and working up by conventional methods. It is also known to take the lactam portions obtained on working up the reaction mixture of the Beckmann rearrangement of cyclohexanone oxime in oleum to lactam, for example the bottoms and first runnings of the lactam distillation, to recycle said lactam portions to the acid rearrangement mixture obtained from the rearrangement of cyclohexanone in oleum, and to work up the resulting mixture (East German Patent No. 73,292).

Another method comprises purifying caprolactam by treatment with oleum followed by distillation (U.K. Patent No. 951,519).

Caprolactam obtained by catalytic gas-phase rearrangement of cyclohexanone oxime, however, contains other impurities than the lactam obtained by Beckmann rearrangement in sulfuric acid or oleum (German Patent Application No. 2,224,505).

Purification of this lactam by extraction and distillation does not provide a product satisfying present-day requirements.

The method described comprises crystallization from a solvent such as water or from the melt, a chemical treatment and/or distillation.

We have now found that it is possible to take caprolactam obtained by catalytic gas-phase rearrangement of cyclohexanone oxime and to work this up together with conventionally prepared caprolactam without the purity of the resulting common lactam being different from that of the lactam obtained in conventional manner, if the crude lactam from the catalytic gas-phase rearrangement of cyclohexanone oxime is added to the acid rearrangement mixture from the Beckmann rearrangement of cyclohexanone oxime in oleum and the resulting mixture is maintained at temperatures of from 100° to 200° C and is then neutralized and worked up.

An advantageous embodiment of this method is described below:

Caprolactam which has been obtained by catalytic gas-phase rearrangement of cyclohexanone oxime in contact with, say, an aluminum oxide/boron oxide catalyst is condensed and then distilled conveniently in vacuum, after the addition of acidic substances such as sulfuric acid, oleum, $NaHSO_4$, $KHSO_4$ and/or after treatment with oxidizing substances such as $Na_2Cr_2O_7$, $CrO_3$, $KMnO_4$ and $H_2O_2$. The resulting lactam is added to an acid rearrangement mixture obtained by a Beckmann rearrangement of cyclohexanone oxime with oleum. The amount of lactam added from the catalytic rearrangement may be up to 50% of the amount of lactam present in the acid rearrangement mixture. It is general to add from about 5 to 30%. The acid rearrangement mixture which now contains lactams from two different synthesis processes, is conveniently maintained, prior to neutralization, at a temperature of from about 100° to 200° C and advantageously from 110° to 150° C for a short period, for example from 5 minutes to 2 hours. The mixture is then neutralized with gaseous or aqueous ammonia to a pH of from about 3.0 to 6.0. The resulting layers are separated and the lacttam phase is extracted in known manner with a solvent such as chlorinated hydrocarbons, for example methylene chloride, chloroform or trichloroethylene, or benzene or toluene. The lactam/solvent phase is distilled to remove the solvent and the lactam is worked up by fractional distillation. The first runnings and bottoms of the fractional distillation may be worked up separately and then returned to the product stream. Alternatively, they may be added to the rearrangement mixture.

There is obtained a pure lactam of a quality equivalent to that of lactam obtained by the conventional method.

Our method of working up lactams from different sources has the advantage that it is possible to purify lactam obtained from the gas-phase rearrangement together with lactam derived from the conventional process. Another advantage is that no new working up technique is required for the lactam obtained from the gas-phase rearrangement. The amount of lactam added from the gas-phase rearrangement requires no additional amounts of sulfuric acid or oleum. On the contrary, the excess of sulfuric acid or oleum already present in the rearrangement mixture is thus utilized for purifying purposes.

The process may be carried out continuously or batchwise.

EXAMPLE 1

100 g of a caprolactam obtained by catalytic gas-phase rearrangement of cyclohexanone oxime in contact with an $Al_2O_3/B_2O_3$ catalyst are added to 2,240 g of a rearrangement mixture obtained by rearrangement of cyclohexanone oxime in oleum and consisting of 1,000 g of lactam and 1,240 g of sulfuric acid and having a free $SO_3$ content of 4% and a small amount of side products. The crude lactam obtained by the catalytic process had the following characteristics:

| | |
|---|---|
| solidification point | 67.9° C |
| color number | more than 1,000 APHA |
| volatile bases | 10.0 meq/kg |
| PAN (permanganate absorption number) | more than 1,000 |

The acid rearrangement mixture is maintained at 130° C for 1 hour and then neutralized with aqueous ammonia to form two layers. The upper crude lactam phase is exhaustively extracted with benzene. There is obtained a benzene phase containing about 15% of lactam. The benzene is separated by distillation and the residue is mixed with 0.2% of caustic soda and fractionally distilled through a column at from 1 to 2 mm of Hg. After the removal of 10% of first runnings, 770 g of center cut are obtained having the following characteristics:

| | |
|---|---|
| solidification point | 69.15° C |
| color number | 2 APHA |
| volatile bases | 0.10 meq/kg |
| PAN | 4.3 |

EXAMPLE 2

300 g of crude lactam obtained from the catalytic gas-phase rearrangement as described in Example 1 are added to 2,240 g rearrangement mixture having the composition described in Example 1. However, before the lactam is added to the rearrangement mixture it is distilled after the addition of 0.5% of sulfuric acid in order to remove some of the impurities such as catalyst dust and high boilers.

The catalytic lactam had the following characteristics:

| | |
|---|---|
| solidification point | 68.9° C |
| color number | about 350 APHA |
| volatile bases | 2.5 meq/kg |
| PAN | about 1,000 |

The acid arrangement mixture is maintained at 135° C for a further 45 minutes with stirring and is then neutralized and worked up. Distillation is again carried out after the addition of 0.2% of caustic soda at a vacuum of from 1 to 2 mm of Hg.

The distillate consists of 890 g of caprolactam having the following characteristics:

| | |
|---|---|
| solidification point | 69.15° C |
| color number | 1 APHA |
| volatile bases | 0.2 meq/kg |
| PAN | 4.0 |

EXAMPLE 3

Crude lactam obtained by catalytic gas-phase rearrangement is distilled without additives. 200 g of this distillate having the following characteristics:

| | |
|---|---|
| solidification point | 68.6° C |
| color number | more than 1,000 APHA |
| volatile bases | 4.0 meq/kg |
| PAN | more than 1,000 | are added to 2,240 g of rearrangement mixture of the composition described in Example 1. The resulting mixture is mantained at 130° C for 30 minutes with stirring and is then neutralized as described in Example 1, extracted and then distilled after the addition of 0.2% of caustic soda.

The distillate obtained consists of 830 g of caprolactam having the following characteristics:

| | |
|---|---|
| solidification point | 69.15° C |
| color number | 3 APHA |
| volatile bases | 0.11 meq/kg |
| PAN | 4.6 |

For purposes of comparison, examples of separate working up are described below:

a. 2,240 g of rearrangement mixture consisting of 1,000 g of lactam and 1,240 g of sulfuric acid and having a free $SO_3$ content of 4% and the resulting side products are worked up in conventional manner without the addition of a lactam from a different source, said working up consisting of neutralization, extraction with benzene and, after removal of the solvent and addition of 0.2% of caustic soda, fractional distillation at from 1 to 2 mm of Hg. The distillate obtained consists of 685 g of caprolactam having the following characteristics:

| | |
|---|---|
| solidification point | 69.15° C |
| color number | 2 APHA |
| volatile bases | 0.12 meq/kg |
| PAN | 4.5 | b. 1,000 g of caprolactam obtained by catalytic gas-phase rearrangement is distilled at from 1 to 2 mm of Hg after the addition of 0.5% of sulfuric acid. The distillate is diluted with water to form a 70% aqueous solution and is then extracted with benzene. After removal of the extracting solvent, the mixture is fractionally distilled after the addition of 0.2% of NaOH.

The center cut had the following characteristics:

| | |
|---|---|
| solidification point | 68.9° C |
| color number | 12 APHA |
| volatile bases | 0,8 meq/kg |
| PAN | 60.2 |

We claim:
1. A method for purifying crude caprolactam obtained in the Beckmann rearrangement of cyclohexanone oxime in oleum together with impure caprolactam obtained from the gas-phase rearrangement of cyclohexanone oxime in the presence of a catalyst, which process comprises adding the impure lactam obtained from the catalytic gas-phase rearrangement of cyclohexanone oxime to an acid rearrangement mixture derived from the Beckmann rearrangement of cyclohexanone oxime in oleum in an amount of said impure lactam up to 50% of the lactam in said acid rearrangement mixture, maintaining the resultant mixture of said lactams at a temperature of 100° to 200° C with thorough stirring of said mixture, then neutralizing said mixture, and recovering substantially pure caprolactam from the neutralized mixture.

2. A method as claimed in claim 1, in which the amount of said impure lactam derived from the catalytic gas-phase rearrangement is added in an amount of 5 to 30% of the amount of lactam in the acid rearrangement mixture obtained from the Beckmann rearrangement.

3. A method as claimed in claim 1 wherein said impure lactam obtained from the catalytic gas-phase rearrangement is distilled in the presence of sulfuric acid or oleum prior to addition to the acid rearrangement mixture.

4. A method as claimed in claim 1 wherein said resultant mixture is maintained at a temperature in the range of 110° to 150° C for 5 minutes to 2 hours.

5. A method as claimed in claim 1 wherein said resultant mixture is maintained at a temperature in the range of 110° to 150° C for 5 minutes to 2 hours, the mixture is then neutralized with gaseous or aqueous ammonia to a pH of about 2.0 to 6.0, and pure caprolactam is obtained by extracting the lactam phase with a solvent, distilling the lactam solvent-phase to remove the solvent, and fractionally distilling the resultant lactam.

* * * * *